US011918939B2

United States Patent
Dubois

(10) Patent No.: US 11,918,939 B2
(45) Date of Patent: Mar. 5, 2024

(54) METHOD FOR PURIFYING HYDROFLUOROCARBONS

(71) Applicant: ARKEMA FRANCE, Colombes (FR)

(72) Inventor: Jean-Luc Dubois, Colombes (FR)

(73) Assignee: ARKEMA FRANCE, Colombes (FR)

(*) Notice: Subject to any disclaimer, the term of this patent is extended or adjusted under 35 U.S.C. 154(b) by 184 days.

(21) Appl. No.: 17/639,357

(22) PCT Filed: Sep. 4, 2020

(86) PCT No.: PCT/EP2020/074781
§ 371 (c)(1),
(2) Date: Mar. 1, 2022

(87) PCT Pub. No.: WO2021/043989
PCT Pub. Date: Mar. 11, 2021

(65) Prior Publication Data
US 2022/0297025 A1 Sep. 22, 2022

(30) Foreign Application Priority Data
Sep. 6, 2019 (FR) ........................ 1909812

(51) Int. Cl.
*B01D 3/08* (2006.01)
*C07C 17/383* (2006.01)

(52) U.S. Cl.
CPC .............. *B01D 3/08* (2013.01); *C07C 17/383* (2013.01)

(58) Field of Classification Search
CPC ................................ B01D 3/08; C07C 17/383
See application file for complete search history.

(56) References Cited

U.S. PATENT DOCUMENTS

| 2016/0317967 A1 | 11/2016 | Kotagiri et al. |
| 2017/0028311 A1 | 2/2017 | Namdeo et al. |
| 2018/0370879 A1 | 12/2018 | Collier et al. |

FOREIGN PATENT DOCUMENTS

| WO | 2017108523 A1 | 6/2017 |
| WO | 2018178554 A1 | 10/2018 |

OTHER PUBLICATIONS

English machine translation of WO 2018/178554 (Year: 2018).*
ISA/EP; International Search Report and Written Opinion for International Patent Application No. PCT/EP2020/074781 dated Dec. 11, 2020, 11 pages.

* cited by examiner

*Primary Examiner* — Renee Robinson
(74) *Attorney, Agent, or Firm* — NK Patent Law

(57) ABSTRACT

The present invention relates to a process for purifying a composition comprising a hydrohalocarbon B comprising the steps of: i) providing a composition A1 comprising a hydrohalocarbon B and at least one impurity C different from said hydrohalocarbon B, ii) compressing said composition A1, and optionally cooling it, so as to obtain said hydrohalocarbon B in liquid form in order to form a liquid stream A2 comprising said hydrohalocarbon B, iii) distilling said stream A2 obtained in step ii) in order to form and recover a stream A3 comprising said hydrohalocarbon B, characterized in that step iii) is carried out in a pressurized distillation device comprising one or more rotating packed beds.

11 Claims, 4 Drawing Sheets

[Fig. 1]
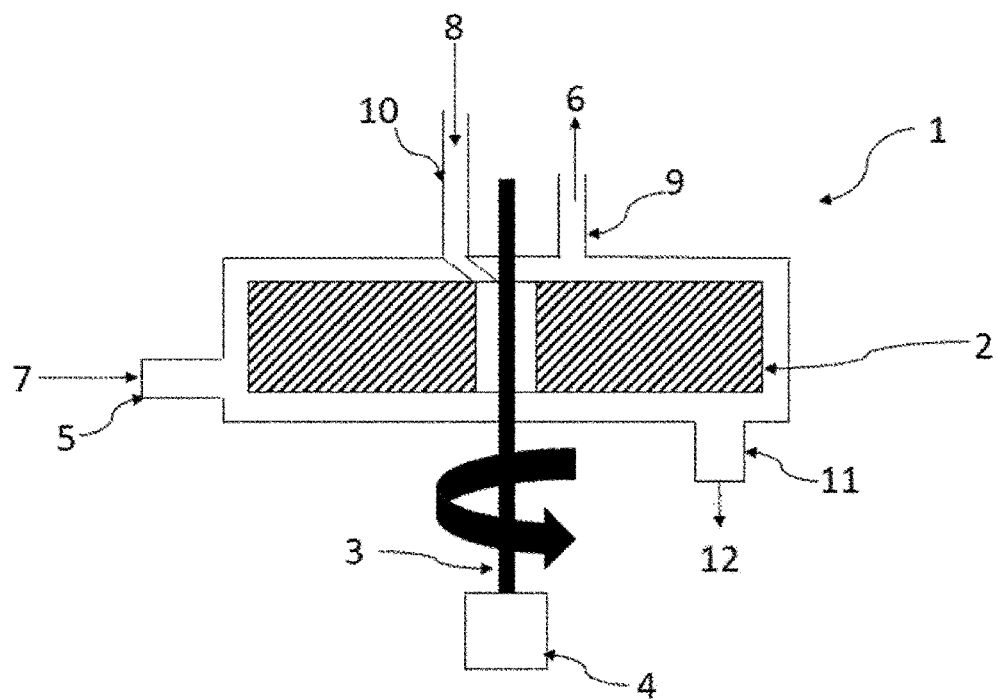

[Fig. 2]
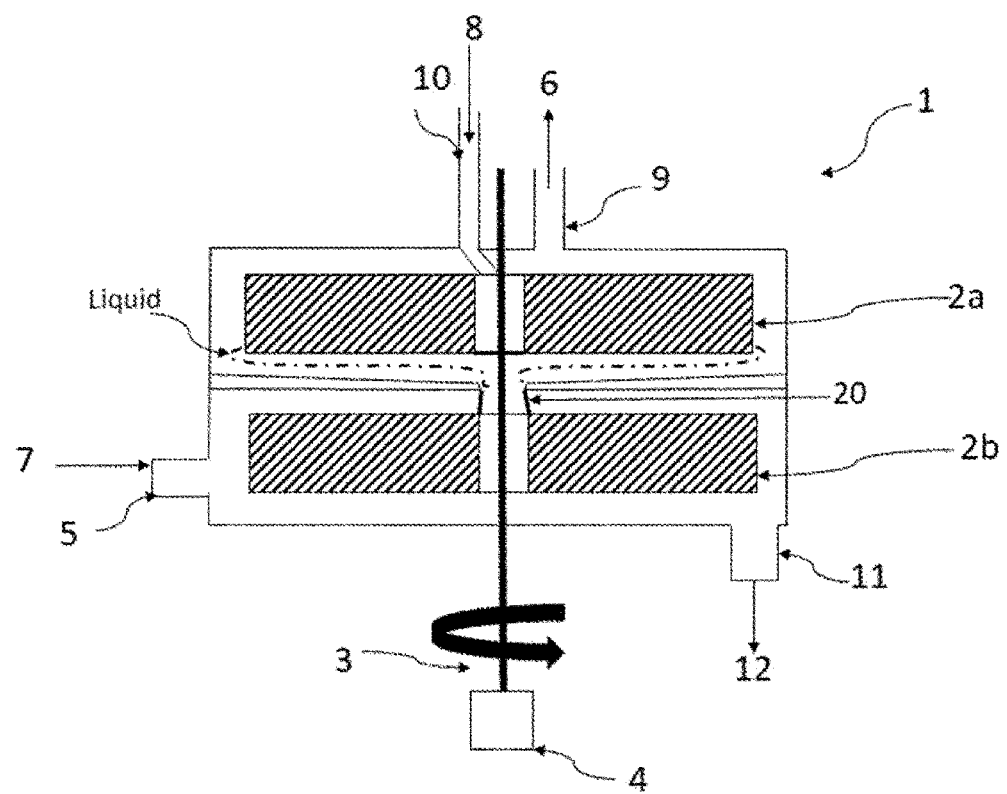

[Fig. 3]
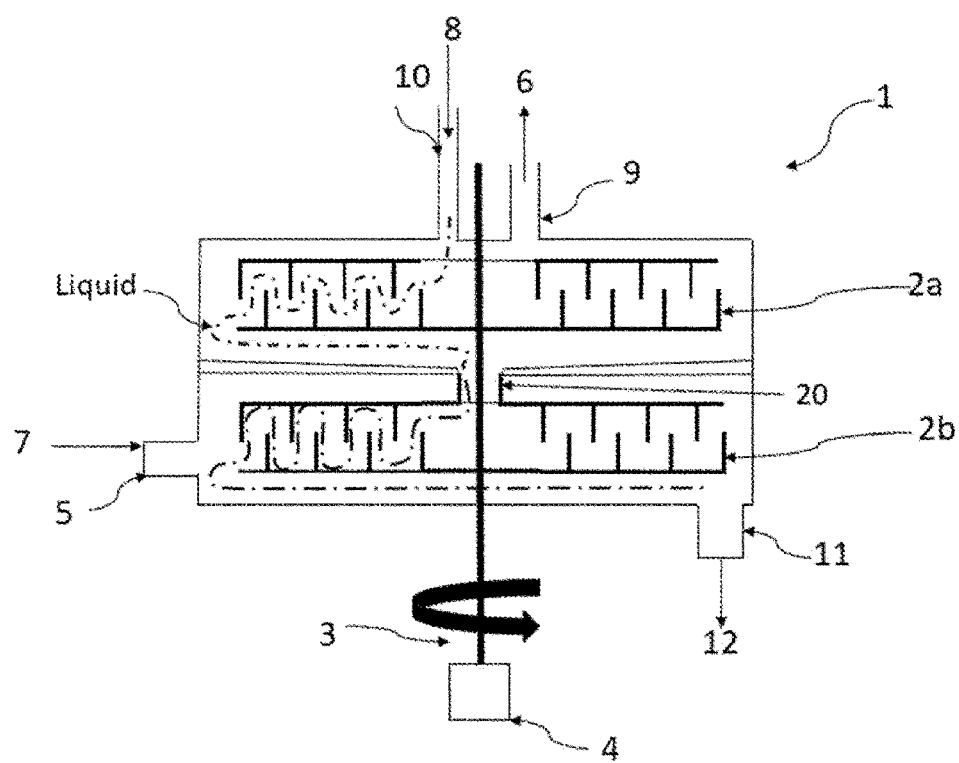

[Fig. 4]
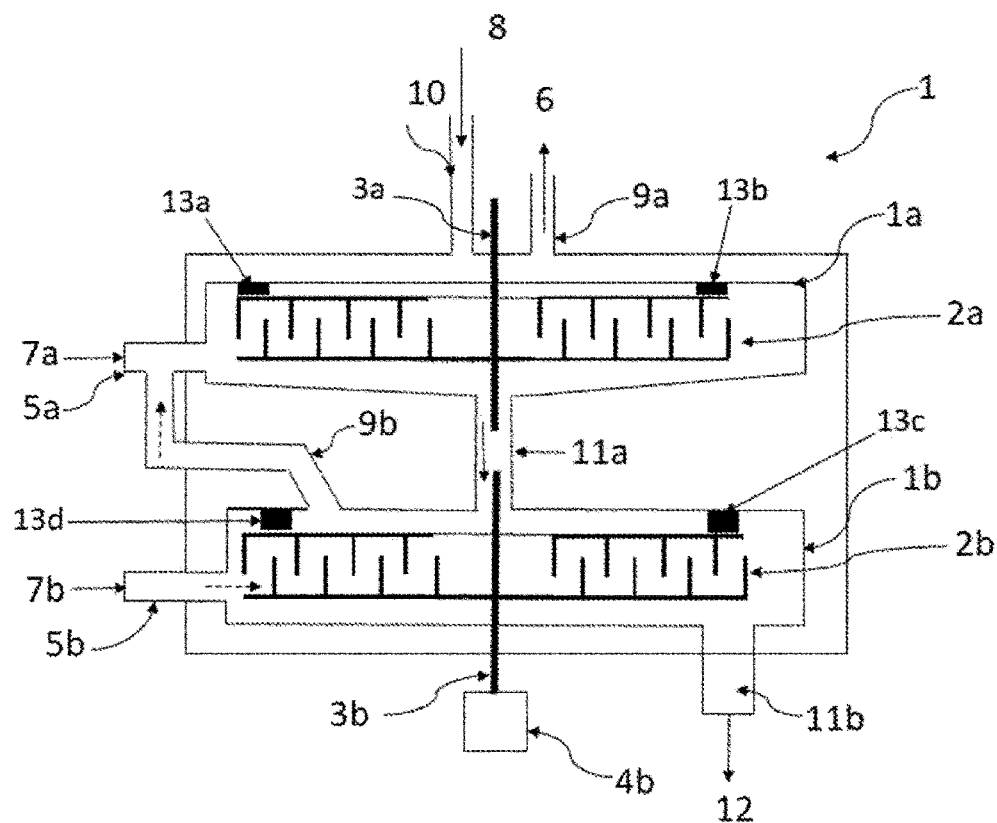

METHOD FOR PURIFYING HYDROFLUOROCARBONS

CROSS-REFERENCE TO RELATED APPLICATIONS

This application is a U.S. National Stage application of International Patent Application No. PCT/EP2020/074781, filed on Sep. 4, 2020, which claims the benefit of French Patent Application No. FR1909812, filed on Sep. 6, 2019.

TECHNICAL FIELD OF THE INVENTION

The present invention relates to a process for purifying hydrohalocarbon compounds. In particular, the present invention relates to a process for purifying hydrohalocarbon compounds by distillation.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as refrigerants and heat-transfer fluids, extinguishers, propellants, foaming agents, blowing agents, gaseous dielectrics, polymerization medium or monomer, support fluids, agents for abrasives, drying agents and fluids for power production units.

HFOs have been identified as desirable alternatives to HCFC as a result of their low ODP (ozone depletion potential) and GWP (global warming potential) values.

Most of the processes for the manufacture of hydrofluoroolefins involve a fluorination and/or dehydrohalogenation reaction. This type of reaction is carried out in the gas phase and generates impurities which consequently have to be removed in order to obtain the desired compound in a sufficient degree of purity for the targeted applications.

Among the routes for obtaining HFO-1234yf, it is in particular known to use HFC-240db (1,1,1,2,3-pentachloropropane) as starting compound. Reference is made, for example, to document WO 2013/088195 in this regard.

Moreover, in the context of producing 2,3,3,3-tetrafluoro-1-propene (HFO-1234yf), the presence of impurities such as 1-chloro-3,3,3-trifluoro-1-propene (1233zd), 1,3,3,3-tetrafluoro-1-propene (1234ze) and 1,1,1,3,3-pentafluoropropane (245fa) is observed. These impurities are isomers of the main compounds that are desired to be obtained via the process for producing 2,3,3,3-tetrafluoro-1-propene, besides the latter, i.e. 2-chloro-3,3,3-trifluoro-1-propene (1233xf) and 1,1,1,2,2-pentafluoropropane (245cb). Given the respective boiling points of 1-chloro-3,3,3-trifluoro-1-propene (1233zd), 1,3,3,3-tetrafluoro-1-propene (1234ze) and 1,1,1,3,3-pentafluoropropane (245fa), they may accumulate in the reaction loop and thus prevent the formation of the products of interest.

The purification of this type of reaction mixture can be carried out by various techniques known from the prior art, such as, for example, distillation. However, when the compounds to be purified have boiling points which are too close or when these form azeotropic or quasi-azeotropic compositions, distillation is not an effective process. Extractive distillation processes have also been described. For example, application WO 2017/108523 describes a process for producing and purifying HFO-1234yf involving a step of extractive distillation.

It is desirable to be able to produce hydrofluoroolefins having a low content of impurities. In particular, the formation of certain impurities which are toxic and/or flammable and/or which are difficult to separate from the desired hydrofluoroolefin should be minimized.

There is therefore a need to provide means for obtaining hydrofluoroolefins, and also the starting materials and the reaction intermediates for obtaining these, of satisfactory purity.

SUMMARY OF THE INVENTION

The present invention relates to a process for purifying a composition comprising a hydrohalocarbon B comprising the steps of:
i) providing a composition A1 comprising a hydrohalocarbon B and at least one impurity C different from said hydrohalocarbon B,
ii) compressing said composition A1, and optionally cooling it, so as to obtain said hydrohalocarbon B in liquid form in order to form a liquid stream A2 comprising said hydrohalocarbon B,
iii) distilling said stream A2 obtained in step ii) in order to form and recover a stream A3 comprising said hydrohalocarbon B,
characterized in that step iii) is carried out in a pressurized distillation device comprising one or more rotating packed beds.

According to a preferred embodiment, said stream A2 is introduced in liquid form into said one or more rotating packed beds and is distributed therein radially with respect to the rotatable shaft thereof.

According to a preferred embodiment, the speed of said one or more rotating packed beds is from 100 to 3000 revolutions per minute (rpm), advantageously from 200 to 2500 rpm, preferably from 500 to 2000 rpm.

According to a preferred embodiment, step iii) is carried out at a pressure of from 2 to 200 bar absolute, preferably from 5 to 100 bar absolute, more preferentially from 5 to 40 bar absolute, in particular from 5 to 30 bar absolute.

According to a preferred embodiment, said hydrohalocarbon B comprises three carbon atoms and at least one halogen atom.

According to a preferred embodiment, said hydrohalocarbon B is of formula (I) $CX(Y)_2—CX(Y)_m—CH_mXY$, where X and Y independently represent H, F or Cl and m=0 or 1 with at least one from among X or Y being Cl or F.

According to a preferred embodiment, said hydrohalocarbon B is selected from the group B1 consisting of 2,3,3,3-tetrafluoropropene, 2-chloro-3,3,3-trifluoropropene, 1,3,3,3-tetrafluoropropene, 1-chloro-3,3,3-trifluoropropene, 1,1,1,2,2-pentafluoropropane, 2-chloro-1,1,1,2-tetrafluoropropane, 2,3-dichloro-1,1,1-trifluoropropane, 3,3,3-trifluoropropene, 1,1,1,3,3-pentafluoropropane, 1,1,1,2,3-pentafluoropropane, 1,1,1,2,3-pentafluoropropene, 1,1,1,2,3-pentachloropropane, 1,1,2,2,3-pentachloropropane, 1,1,1,3,3-pentachloropropane, 1,1,2,3-tetrachloro-1-propene, 2,3,3,3-tetrachloro-1-propene, 1,1,3,3-tetrachloro-1-propene and 1,3,3,3-tetrachloro-1-propene.

According to a preferred embodiment, said at least one impurity C is selected from the group C1 consisting of chloromethane, dichloromethane, tetrachloromethane, trichlorofluoromethane, dichlorodifluoromethane, trichlorotrifluoroethane, dichlorotetrafluoroethane, chloropentafluoroethane, fluoromethane, difluoromethane, trifluoromethane, fluoroethane, 1,1-difluoroethane, 1,2-difluoroethane, 1,1,1-trifluoroethane, 1,1,2-trifluoroethane, 3,3,3-trifluoropropyne, methane, ethane, propane, 1,1,1-trifluoroethane, 1,1,1,2,3,3,3-heptachloropropane, 1,1,1,2,2,3,3-heptachloropropane, 2-chloro-1,1,1,3,3,3-hexafluoropropane, 1-chloro-1,1,2,3,3,3-hexafluoropropane, 2-chloro-1,1,2,3,3, 3-hexafluoropropane, 3-chloro-1,1,1,2,2,3-hexafluoropropane, 1-chloro-1,1,2,2,3,3-hexafluoropropane, 1,1,1,3,3,3-hexachloropropane, 1,1,1,2,3,3-hexachloropropane, 1,1,2,2, 3,3-hexachloropropane, 1,1,1,2,2,3-hexachloropropane, 3-chloro-1,1,1,3,3-pentafluoropropane, 1-chloro-1,2,3,3,3-pentafluoropropane, 1-chloro-1,1,2,3,3-pentafluoropropane, 3-chloro-1,1,2,2,3-pentafluoropropane, 3-chloro-1,1,1,2,2-pentafluoropropane, 1-chloro-1,1,2,2,3-pentafluoropropane, 2-chloro-1,1,1,3,3-pentafluoropropane, 2-chloro-1,1,2,3,3-pentafluoropropane, 2-chloro-1,1,1,2,3-pentafluoropropane, 1,1,1,3,3,3-hexafluoropropane, 1,1,2,2,3,3-hexafluoropropane, 1,1,1,2,2,3-hexafluoropropane, 1,1,1,2,3,3-hexafluoropropane, 1,1,1,3,3-pentachloropropane, 1,1,2,3,3-pentachloropropane, 1,1,1,2,3-pentachloropropane, 1,1,2,2,3-pentachloropropane, 1,1,1,2,2-pentachloropropane, 1,1,2,2, 3-pentafluoropropane, 1,1,1,2,2-pentafluoropropane, 1,1,2, 3,3-pentafluoropropane, 1,1,1,2,3-pentafluoropropane, 1,1, 3,3-pentafluoropropane, 1,1,3,3-tetrachloropropane, 1,1,1, 3-tetrachloropropane, 1,1,2,3-tetrachloropropane, 1,1,1,2-tetrachloropropane, 1,2,2,3-tetrachloropropane, 1,1,2,2-tetrachloropropane, 1-chloro-1,1,3-trifluoropropane, 1-chloro-3,3,3-trifluoropropane, 1-chloro-1,1,3-trifluoropropane, 2-chloro-1,2,3-trifluoropropane, 2-chloro-1,1,2-trifluoropropane, 1-chloro-2,2,3-trifluoropropane, 1-chloro-1, 2,2-trifluoropropane, 3-chloro-1,1,2-trifluoropropane, 1-chloro-1,2,3-trifluoropropane, 1-chloro-1,1,2-trifluoropropane, 1,1,3-trichloropropane, 1,1,1-trichloropropane, 1,2,3-trichloropropane, 1,1,2-trichloropropane, 1,2,2-trichloropropane, hexachloropropene, 1,1,2-trichloro-3,3,3-trifluoropropene, 1,2,3-trichloro-1,3,3-trifluoropropene, 2,3, 3-trichloro-1,1,3-trifluoropropene, 3,3,3-trichloro-1,1,2-trifluoropropene, 1,3,3-trichloro-1,2,3-trifluoropropene, 1,1, 3-trichloro-2,3,3-trifluoropropene, 3,3-dichloro-1,1,2,3-tetrafluoropropene, 2,3-dichloro-1,1,3,3-tetrafluoropropene, 1,3-dichloro-1,2,3,3-tetrafluoropropene, 1,2-dichloro-1,3,3, 3-tetrafluoropropene, 1,2-dichloro-2,3,3,3-tetrafluoropropene, hexafluoropropene, 1,1,2,3,3-pentachloropropene, 1,2,3,3,3-pentachloropropene, 1,1,3,3,3-pentachloropropene, 1,2-dichloro-3,3,3-trifluoropropene, 2,3-dichloro-1,3, 3-trifluoropropene, 2,3-dichloro-1,1,3-trifluoropropene, 3,3-dichloro-1,1,3-trifluoropropene, 1,3-dichloro-1,3,3-trifluoropropene, 1,1-dichloro-3,3,3-trifluoropropene, 1,1-dichloro-2,3,3-trifluoropropene, 1,3-dichloro-2,3,3-trifluoropropene, 3,3-dichloro-1,2,3-trifluoropropene, 3,3-dichloro-1,1,2-trifluoropropene, 3-chloro-1,1,2,3-tetrafluoropropene, 2-chloro-1,1,3,3-tetrafluoropropene, 3-chloro-1,1,3,3-tetrafluoropropene, 1-chloro-1,2,3,3-tetrafluoropropene, 1-chloro-1,3,3,3-tetrafluoropropene, 3-chloro-1,2,3,3-tetrafluoropropene, 2-chloro-1,3,3,3-tetrafluoropropene, 1-chloro-2,3,3,3-tetrafluoropropene, 1,1,3, 3,3-pentafluoropropene, 1,1,2,3,3-pentafluoropropene, 1,2, 3,3,3-pentafluoropropene, 1,1,2,3-tetrachloropropene, 1,2,3, 3-tetrachloropropene, 2,3,3,3-tetrachloropropene, 1,1,3,3-tetrachloropropene, 1,3,3,3-tetrachloropropene, 2-chloro-3, 3,3-trifluoropropene, 3-chloro-2,3,3-trifluoropropene, 1-chloro-2,3,3-trifluoropropene, 1-chloro-3,3,3-trifluoropropene, 2-chloro-1,3,3-trifluoropropene, 3-chloro-1,2,3-trifluoropropene, 3-chloro-1,3,3-trifluoropropene, 3-chloro-1, 1,2-trifluoropropene, 2-chloro-1,1,3-trifluoropropene, 3-chloro-1,1,3-trifluoropropene, 1-chloro-1,2,3-trifluoropropene, 1-chloro-1,3,3-trifluoropropene, 2,3,3,3-tetrafluoropropene, 1,3,3,3-tetrafluoropropene, 1,1,2,3-tetrafluoropropene, 1,1,3,3-tetrafluoropropene, 1,2,3,3-tetrafluoropropene, 1,1,2-trichloropropene, 1,2,3-trichloropropene, 2,3,3-trichloropropene, 1,1,3-trichloropropene, 1,3,3-trichloropropene, 3,3,3-trichloropropene, 3-chloro-3,3-difluoropropene, 3-chloro-2, 3-difluoropropene, 2-chloro-3,3-difluoropropene, 2-chloro-1,1-difluoropropene, 3-chloro-1,1-difluoropropene, 3-chloro-1,2-difluoropropene, 2-chloro-1,3-difluoropropene, 3-chloro-1,3-difluoropropene, 1-chloro-2,3-difluoropropene, 1-chloro-3,3-difluoropropene, 1,1,3-trifluoropropene, 1,1,2-trifluoropropene, 3,3,3-trifluoropropene, 1,2,3-trifluoropropene, 2,3,3-trifluoropropene, 1,3,3-trifluoropropene, 1,1-dichloropropene, 1,2-dichloropropene, 2,3-dichloropropene, 1,3-dichloropropene, 3,3-dichloropropene, 1,1-difluoropropene, 1,2-difluoropropene, 2,3-difluoropropene and 3,3-difluoropropene.

According to a preferred embodiment, said stream A3 comprises said hydrohalocarbon B in a weight content of greater than 90% by weight on the basis of the total weight of said stream A3. According to a preferred embodiment, in said stream A3 the content of said at least one impurity C is less than 1% by weight.

According to a preferred embodiment, said pressurized distillation device comprises an inlet enabling it to be fed with a stream sweeping said rotating packed bed countercurrently.

The present invention makes it possible to separate hydrohalocarbon constituents more effectively than with cryogenic distillation apparatus. The cryogenic distillation of hydrofluorocarbon compounds requires a very low distillation temperature given the boiling points of these compounds and even sizeable apparatus given the similar boiling points of these various components. The present invention provides a surprising process that makes it possible to use apparatus that is more compact and less energy-consuming since the process can be carried out at temperatures close to ambient owing to the use of the pressurized device (the temperature of the device can moreover be regulated with water rather than with other refrigerant mixtures). The use of a pressurized and rotating device makes it possible to separate the constituents of the stream owing to centrifugal force and makes it possible to avoid the formation of azeotropes often present with hydrohalocarbon compounds.

BRIEF DESCRIPTION OF THE FIGURES

FIG. 1 represents a schematic view of a pressurized distillation device comprising one rotating packed bed according to a particular embodiment of the invention.

FIG. 2 represents a schematic view of a pressurized distillation device comprising two rotating packed beds according to a particular embodiment of the invention.

FIG. 3 represents a schematic view of a pressurized distillation device comprising two rotating packed beds according to another particular embodiment of the invention.

FIG. 4 represents a schematic view of a pressurized distillation device comprising two rotating packed beds operating at different pressures according to a particular embodiment of the invention.

DETAILED DESCRIPTION OF THE INVENTION

The present invention relates to a process for purifying a composition comprising a hydrohalocarbon B.

Preferably, said process comprises the step of:

i) providing a composition A1 comprising a hydrohalocarbon B and at least one impurity C different from said hydrohalocarbon compound B.

Preferably, said hydrohalocarbon compound B comprises from 1 to 10 carbon atoms, more preferentially said hydrohalocarbon compound B comprises from 2 to 9 carbon atoms, in particular from 2 to 8 carbon atoms, more particularly from 2 to 7 carbon atoms.

Preferably, said hydrohalocarbon compound B comprises at least one halogen atom. Preferably, said hydrohalocarbon compound B comprises two, three, four, five, six, seven, eight, nine or ten halogen atoms. In particular, the halogen atom is F or Cl.

Preferably, said hydrohalocarbon compound B comprises from 1 to 10 carbon atoms, more preferentially said hydrohalocarbon compound B comprises from 2 to 9 carbon atoms, in particular from 2 to 8 carbon atoms, more particularly from 2 to 7 carbon atoms and at least one halogen atom, advantageously two, three, four, five, six, seven, eight, nine or ten halogen atoms; the halogen atom being F or Cl.

According to a preferred embodiment, said hydrohalocarbon B comprises three carbon atoms and at least one halogen atom. Preferably, said hydrohalocarbon B comprises three carbon atoms and 2 to 7 halogen atoms selected from F and Cl.

According to a preferred embodiment, said hydrohalocarbon B is of formula (I) $CX(Y)_2$—$CX(Y)_m$—$CH_mXY$, where X and Y independently represent H, F or Cl and m=0 or 1 with at least one from among X or Y being Cl or F.

According to a preferred embodiment, said hydrohalocarbon B is selected from the group B1 consisting of 2,3,3,3-tetrafluoropropene, 2-chloro-3,3,3-trifluoropropene, 1,3,3,3-tetrafluoropropene, 1-chloro-3,3,3-trifluoropropene, 1,1,1,2,2-pentafluoropropane, 2-chloro-1,1,1,2-tetrafluoropropane, 2,3-dichloro-1,1,1-trifluoropropane, 3,3,3-trifluoropropene, 1,1,1,3,3-pentafluoropropane, 1,1,1,2,3-pentafluoropropane, 1,1,1,2,3-pentafluoropropene, 1,1,1,2,3-pentachloropropane, 1,1,2,2,3-pentachloropropane, 1,1,1,3,3-pentachloropropane, 1,1,2,3-tetrachloro-1-propene, 2,3,3,3-tetrachloro-1-propene, 1,1,3,3-tetrachloro-1-propene and 1,3,3,3-tetrachloro-1-propene.

Said at least one impurity C comprises from 1 to 10 carbon atoms, advantageously from 2 to 9 carbon atoms, preferably from 2 to 8 carbon atoms, in particular from 2 to 7 carbon atoms. Said at least one impurity C may comprise one or more halogen atoms on its carbon chain, preferably the halogen atom is chosen from Cl or F.

Preferably, said at least one impurity C is selected from the group C1 consisting of chloromethane, dichloromethane, tetrachloromethane, trichlorofluoromethane, dichlorodifluoromethane, trichlorotrifluoroethane, dichlorotetrafluoroethane, chloropentafluoroethane, fluoromethane, difluoromethane, trifluoromethane, fluoroethane, 1,1-difluoroethane, 1,2-difluoroethane, 1,1,1-trifluoroethane, 1,1,2-trifluoroethane, 3,3,3-trifluoropropyne, methane, ethane, propane, 1,1,1-trifluoroethane, 1,1,1,2,3,3,3-heptachloropropane, 1,1,1,2,2,3,3-heptachloropropane, 2-chloro-1,1,1,3,3,3-hexafluoropropane, 1-chloro-1,1,2,3,3,3-hexafluoropropane, 2-chloro-1,1,2,3,3,3-hexafluoropropane, 3-chloro-1,1,1,2,2,3-hexafluoropropane, 1-chloro-1,1,2,2,3,3-hexafluoropropane, 1,1,1,3,3,3-hexachloropropane, 1,1,1,2,3,3-hexachloropropane, 1,1,2,2,3,3-hexachloropropane, 1,1,1,2,2,3-hexachloropropane, 3-chloro-1,1,1,3,3-pentafluoropropane, 1-chloro-1,2,3,3,3-pentafluoropropane, 1-chloro-1,1,2,3,3-pentafluoropropane, 3-chloro-1,1,2,2,3-pentafluoropropane, 3-chloro-1,1,1,2,2-pentafluoropropane, 1-chloro-1,1,2,2,3-pentafluoropropane, 2-chloro-1,1,1,3,3-pentafluoropropane, 2-chloro-1,1,2,3,3-pentafluoropropane, 2-chloro-1,1,1,2,3-pentafluoropropane, 1,1,1,3,3,3-hexafluoropropane, 1,1,2,2,3,3-hexafluoropropane, 1,1,1,2,2,3-hexafluoropropane, 1,1,1,2,3,3-hexafluoropropane, 1,1,1,2,3,3-pentachloropropane, 1,1,1,3,3-pentachloropropane, 1,1,2,3,3-pentachloropropane, 1,1,1,2,3-pentachloropropane, 1,1,2,2,3-pentachloropropane, 1,1,1,2,2-pentachloropropane, 1,1,2,2,3-pentafluoropropane, 1,1,1,2,2-pentafluoropropane, 1,1,2,3,3-pentafluoropropane, 1,1,1,2,3-pentafluoropropane, 1,1,1,3,3-pentafluoropropane, 1,1,3,3-tetrachloropropane, 1,1,1,3-tetrachloropropane, 1,1,2,3-tetrachloropropane, 1,1,1,2-tetrachloropropane, 1,2,2,3-tetrachloropropane, 1,1,2,2-tetrachloropropane, 1-chloro-1,1,3-trifluoropropane, 1-chloro-3,3,3-trifluoropropane, 1-chloro-1,1,3-trifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 1,1,3-trichloropropane, 1,1,1-trichloropropane, 1,2,3-trichloropropane, 1,1,2-trichloropropane, 1,2,2-trichloropropane, hexachloropropene, 1,1,2-trichloro-3,3,3-trifluoropropene, 1,2,3-trichloro-1,3,3-trifluoropropene, 2,3,3-trichloro-1,1,3-trifluoropropene, 3,3,3-trichloro-1,1,2-trifluoropropene, 1,3,3-trichloro-1,2,3-trifluoropropene, 1,1,3-trichloro-2,3,3-trifluoropropene, 3,3-dichloro-1,1,2,3-tetrafluoropropene, 2,3-dichloro-1,1,3,3-tetrafluoropropene, 1,3-dichloro-1,2,3,3-tetrafluoropropene, 1,2-dichloro-1,3,3,3-tetrafluoropropene, 1,2-dichloro-2,3,3,3-tetrafluoropropene, hexafluoropropene, 1,1,2,3,3-pentachloropropene, 1,2,3,3,3-pentachloropropene, 1,1,3,3,3-pentachloropropene, 1,2-dichloro-3,3,3-trifluoropropene, 2,3-dichloro-1,3,3,3-trifluoropropene, 2,3-dichloro-1,1,3-trifluoropropene, 3,3-dichloro-1,1,3-trifluoropropene, 1,3-dichloro-1,3,3-trifluoropropene, 1,1-dichloro-3,3,3-trifluoropropene, 1,1-dichloro-2,3,3-trifluoropropene, 1,3-dichloro-2,3,3-trifluoropropene, 3,3-dichloro-1,2,3-trifluoropropene, 3,3-dichloro-1,1,2-trifluoropropene, 3-chloro-1,1,2,3-tetrafluoropropene, 2-chloro-1,1,3,3-tetrafluoropropene, 3-chloro-1,1,3,3-tetrafluoropropene, 1-chloro-1,2,3,3-tetrafluoropropene, 1-chloro-1,3,3,3-tetrafluoropropene, 3-chloro-1,2,3,3-tetrafluoropropene, 2-chloro-1,3,3,3-tetrafluoropropene, 1-chloro-2,3,3,3-tetrafluoropropene, 1,1,3,3,3-pentafluoropropene, 1,1,2,3,3-pentafluoropropene, 1,2,3,3,3-pentafluoropropene, 1,1,2,3-tetrachloropropene, 1,2,3,3-tetrachloropropene, 2,3,3,3-tetrachloropropene, 1,1,3,3-tetrachloropropene, 1,3,3,3-tetrachloropropene, 2-chloro-3,3,3-trifluoropropene, 3,3-trifluoropropene, 3-chloro-2,3,3-trifluoropropene, 1-chloro-2,3,3-trifluoropropene, 1-chloro-3,3,3-trifluoropropene, 2-chloro-1,3,3-trifluoropropene, 3-chloro-1,2,3-trifluoropropene, 3-chloro-1,3,3-trifluoropropene, 3-chloro-1,2-trifluoropropene, 2-chloro-1,1,3-trifluoropropene, 3-chloro-1,1,3-trifluoropropene, 1-chloro-1,2,3-trifluoropropene, 1-chloro-1,3,3-trifluoropropene, 2,3,3,3-tetrafluoropropene, 1,3,3,3-tetrafluoropropene, 1,1,2,3-tetrafluoropropene, 1,1,3,3-tetrafluoropropene, 1,2,3,3-tetrafluoropropene, 1,1,2-trichloropropene, 1,2,3-trichloropropene, 2,3,3-trichloropropene, 1,1,3-trichloropropene, 1,3,3-trichloropropene, 3,3,3-trichloropropene, 3-chloro-3,3-difluoropropene, 3-chloro-2,3-difluoropropene, 2-chloro-3,3-difluoropropene, 2-chloro-1,1-difluoropropene, 3-chloro-1,1-difluoropropene, 3-chloro-1,2-difluoropropene, 2-chloro-1,3-difluoropropene, 3-chloro-1,3-difluoropropene, 1-chloro-2,3-difluoropropene, 1-chloro-3,3-difluoropropene, 1,1,3-trifluoropropene, 1,1,2-trifluoropropene, 3,3,3-trifluoropropene, 1,2,3-trifluoropropene, 2,3,3-trifluoropropene, 1,3,3-trifluoropropene, 1,1-dichloropropene, 1,2-dichloropropene, 2,3-dichloropropene, 1,3-dichloropropene, 3,3-dichloropropene, 1,1-difluoropropene, 1,2-difluoropropene, 2,3-difluoropropene and 3,3-difluoropropene.

Preferably, said composition A1 comprises a hydrohalocarbon B selected from the group B1 as defined above; and at least one impurity C selected from the group C1 as defined above. Preferably, said composition A1 comprises a hydrohalocarbon B selected from the group B1 as defined above and at least two impurities C selected from the group C1 as defined above, said impurities C being different from said hydrohalocarbon B.

Preferably, said composition A1 comprises a hydrohalocarbon B selected from the group B1 as defined above; and at least three, advantageously at least four, preferably at least five, more preferentially at least six, in particular at least seven, more particularly at least eight, favorably at least nine, preferentially favorably at least ten impurities C selected from the group C1 as defined above, said impurities C being different from said hydrohalocarbon B.

Preferably, said composition A1 comprises a hydrohalocarbon B selected from the group B2 consisting of 2,3,3,3-tetrafluoropropene, 2-chloro-3,3,3-trifluoropropene, 1,3,3,3-tetrafluoropropene, 1-chloro-3,3,3-trifluoropropene, 1,1,1,2,3-pentafluoropropene; and at least one, advantageously at least two, preferably at least three, more preferentially at least four, in particular at least five, more particularly at least six, favorably at least seven, advantageously favorably at least eight, preferentially favorably at least nine, particularly favorably at least ten impurities C selected from the group C2 consisting of chloromethane, 3,3,3-trifluoropropyne, 1,1,1-trifluoroethane, 1,1,1,3,3,3-hexafluoropropane, 1,1,2,2,3,3-hexafluoropropane, 1,1,1,2,2,3-hexafluoropropane, 1,1,1,2,3,3-hexafluoropropane, 1,1,1,3,3-pentachloropropane, 1,1,2,3,3-pentachloropropane, 1,1,1,2,3-pentachloropropane, 1,1,2,2,3-pentachloropropane, 1,1,1,2,2-pentachloropropane, 1,1,2,2,3-pentafluoropropane, 1,1,1,2,2-pentafluoropropane, 1,1,2,2,3-pentafluoropropane, 1,1,1,2,3-pentafluoropropane, 1,1,1,3,3-pentafluoropropane, 1,1,3,3-tetrachloropropane, 1,1,1,3-tetrachloropropane, 1,1,2,3-tetrachloropropane, 1,1,1,2-tetrachloropropane, 1,2,2,3-tetrachloropropane, 1,1,2,2-tetrachloropropane, 1,1,3-trichloropropane, 1,1,1-trichloropropane, 1,2,3-trichloropropane, 1,1,2-trichloropropane, 1,2,2-trichloropropane, hexafluoropropene, 1,1,3,3,3-pentafluoropropene, 1,1,2,3,3-pentafluoropropene, 1,2,3,3,3-pentafluoropropene, 1,1,2,3-tetrachloropropene, 1,2,3,3-tetrachloropropene, 2,3,3,3-tetrachloropropene, 1,1,3,3-tetrachloropropene, 1,3,3,3-tetrachloropropene, 2-chloro-3,3-trifluoropropene, 3-chloro-2,3,3-trifluoropropene, 1-chloro-2,3,3-trifluoropropene, 1-chloro-3,3,3-trifluoropropene, 2-chloro-1,3,3-trifluoropropene, 3-chloro-1,2,3-trifluoropropene, 3-chloro-1,3,3-trifluoropropene, 3-chloro-1,1,2-trifluoropropene, 2-chloro-1,1,3-trifluoropropene, 3-chloro-1,1,3-trifluoropropene, 1-chloro-1,2,3-trifluoropropene, 1-chloro-1,3,3-trifluoropropene, 2,3,3,3-tetrafluoropropene, 1,3,3,3-tetrafluoropropene, 1,1,2,3-tetrafluoropropene, 1,1,3,3-tetrafluoropropene, 1,2,3,3-tetrafluoropropene, 1,1,3-trifluoropropene, 1,1,2-trifluoropropene, 3,3,3-trifluoropropene, 1,2,3-trifluoropropene, 2,3,3-trifluoropropene and 1,3,3-trifluoropropene; said impurity or impurities C being different from said hydrohalocarbon B.

Preferably, said composition A1 comprises at least 20% by weight of said hydrohalocarbon B on the basis of the total weight of said composition. In particular, said composition A1 comprises at least 22%, at least 24%, at least 26%, at least 28%, at least 30%, at least 32%, at least 34%, at least 36%, at least 38%, at least 40%, at least 42%, at least 44%, at least 46%, at least 48%, at least 50%, at least 52%, at least 54%, at least 56%, at least 58%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 96%, at least 98% by weight of said hydrohalocarbon B on the basis of the total weight of said composition.

Preferably, said composition A1 comprises less than 80% by weight of said at least one impurity C on the basis of the total weight of said composition. When the composition A1 comprises several impurities C, the content mentioned above is that of all the impurities C included in said composition A1. In particular, said composition A1 comprises less than 78%, less than 76%, less than 74%, less than 72%, less than 70%, less than 68%, less than 66%, less than 64%, less than 62%, less than 60%, less than 58%, less than 56%, less than 54%, less than 52%, less than 50%, less than 48%, less than 46%, less than 44%, less than 42%, less than 40%, less than 38%, less than 36%, less than 34%, less than 32%, less than 30%, less than 28%, less than 26%, less than 24%, less than 22%, less than 20%, less than 18%, less than 16%, less than 14%, less than 12%, less than 10%, less than 8%, less than 6%, less than 4%, less than 2% by weight of said at least one (of said) impurity (impurities) C on the basis of the total weight of said composition.

According to the present process, said composition A1 is compressed. Preferably, said composition A1 is compressed and then cooled to a temperature such that said hydrohalocarbon B is in liquid form. Thus, said hydrohalocarbon B is in liquid form before the implementation of step iii). During step ii), said at least one impurity C can also be in liquid form. If the composition A1 comprises several impurities C, all or some of said impurities C can be in liquid form. Thus, during the implementation of step ii), all or some of the composition A1 may be in liquid form. A person skilled in the art, owing to their general knowledge, will adapt the temperature to the pressure chosen to compress said composition A1 in order to obtain said hydrohalocarbon B in liquid form.

Preferably, during step ii), said composition A1 is compressed under a pressure of from 2 bar absolute to 200 bar absolute, preferably from 5 to 100 bar absolute, more preferentially from 5 to 40 bar absolute, in particular from 5 to 30 bar absolute. Preferably, said composition A1 is compressed to a pressure greater than or equal to the pressure at which step iii) is carried out. The compression can be carried out stepwise to achieve a pressure greater than or equal to the pressure at which step iii) is carried out. During this compression step, an intermediate withdrawal of one or more impurities C as defined in the present application can be carried out. The implementation of step ii) enables the formation of a stream A2 comprising said hydrohalocarbon B selected from the group B1 or B2 as defined above. Preferably, the stream A2 is in liquid form. Said stream A2 may also comprise one or more impurities C selected from the group C1 or C2 as defined above; these being preferably in liquid form. Alternatively, the stream A2 may comprise a liquid phase and a gas phase; said liquid phase comprising said hydrohalocarbon B selected from the group B1 or B2 as defined above and optionally one or more impurities C selected from the group C1 or C2 as defined above being in liquid form under the temperature and pressure conditions chosen for the implementation of step ii). Said gas phase may comprise one or more impurities C selected from the group C1 or C2 as defined above being in gaseous form under the temperature and pressure conditions chosen for the implementation of step ii).

Preferably, said stream A2 comprises said hydrohalocarbon B selected from the group B1 as defined above; and said at least one impurity C selected from the group C1 as defined above. Preferably, said stream A2 comprises said hydrohalocarbon B selected from the group B1 as defined above and said at least two impurities C selected from the group C1 as defined above, said impurities C being different from said hydrohalocarbon B.

Preferably, said stream A2 comprises said hydrohalocarbon B selected from the group B1 as defined above; and said at least three, advantageously at least four, preferably at least five, more preferentially at least six, in particular at least seven, more particularly at least eight, favorably at least nine, preferentially favorably at least ten impurities C selected from the group C1 as defined above.

Preferably, said stream A2 comprises said hydrohalocarbon B selected from the group B2 as defined above; and said at least one, advantageously at least two, preferably at least three, more preferentially at least four, in particular at least five, more particularly at least six, favorably at least seven, advantageously favorably at least eight, preferentially favorably at least nine, particularly favorably at least ten impurities C selected from the group C2 as defined above; said impurity or impurities C being different from said hydrohalocarbon B.

Preferably, said stream A2 comprises at least 20% by weight of said hydrohalocarbon B on the basis of the total weight of said stream. In particular, said stream A2 comprises at least 22%, at least 24%, at least 26%, at least 28%, at least 30%, at least 32%, at least 34%, at least 36%, at least 38%, at least 40%, at least 42%, at least 44%, at least 46%, at least 48%, at least 50%, at least 52%, at least 54%, at least 56%, at least 58%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 96%, at least 98% by weight of said hydrohalocarbon B on the basis of the total weight of said stream.

Preferably, said stream A2 comprises less than 80% by weight of said at least one impurity C on the basis of the total weight of said stream. When said stream A2 comprises several impurities C, the content mentioned above is that of all the impurities C included in said stream A2. In particular, said stream A2 comprises less than 78%, less than 76%, less than 74%, less than 72%, less than 70%, less than 68%, less than 66%, less than 64%, less than 62%, less than 60%, less than 58%, less than 56%, less than 54%, less than 52%, less than 50%, less than 48%, less than 46%, less than 44%, less than 42%, less than 40%, less than 38%, less than 36%, less than 34%, less than 32%, less than 30%, less than 28%, less than 26%, less than 24%, less than 22%, less than 20%, less than 18%, less than 16%, less than 14%, less than 12%, less than 10%, less than 8%, less than 6%, less than 4%, less than 2% by weight of said at least one (of said) impurity (impurities) C on the basis of the total weight of said stream A2.

The present process also comprises a step of:
iii) distilling said stream A2 obtained in step ii) in order to form and recover a stream A3 comprising said hydrohalocarbon B. Thus, said stream A2 obtained in step ii) is distilled under conditions suitable for forming and recovering a stream A3 comprising said hydrohalocarbon B. The implementation of step iii) also makes it possible to recover a stream A4 which comprises at least a portion, preferably all, of said at least one impurity C present in said stream A2. Preferably, said step iii) is carried out in a pressurized distillation device comprising one or more rotating packed beds in which the centrifugal force replaces the force of gravity of a conventional distillation column. Said pressurized distillation device may comprise two, three, four, five, six, seven, eight, nine, ten or more than ten rotating packed beds. Said rotating packed beds may be arranged in cascade or in separate compartments within said pressurized distillation device. Each of said rotating packed beds may have the same pressure or different pressures. FIG. 1 schematically illustrates a pressurized distillation device 1 comprising a rotating packed bed 2. Said rotating packed bed is connected to a shaft 3 connected to a motor 4 enabling the rotation of said rotating packed bed around the shaft 3. The shaft 3 and the motor 4 make it possible to regulate the speed of rotation of said rotating packed bed 2. The rotating packed bed can have various configurations known to those skilled in the art, making it possible to have sufficient permeability to the liquid stream and to the gas stream in order to optimize their circulation within the rotating packed bed 2. Applications US 2017/0028311 and US 2016/0317967 describe in particular rotating packed beds with various configurations. Said pressurized distillation device 1 also comprises a first inlet 10 for supplying said pressurized distillation device 1 with a stream 8 that is liquid or at least partially liquid. Preferably, said first inlet 10 makes it possible to supply said pressurized distillation device 1 with said stream A2 as defined in the present application. Said pressurized distillation device 1 also comprises a second inlet 5 for supplying said pressurized distillation device 1 with a stream 7. Preferably, said second inlet 5 is positioned at the periphery of the pressurized distillation device 1, in order to sweep said rotating packed bed 2 countercurrently. The stream 7 can be a solvent or an inert gas such as for example nitrogen or air. Said solvent can be an organic extraction agent capable of solubilizing one or more impurities C contained in said stream A2. The addition of an inert gas during the distillation makes it possible to promote the separation between the various constituents of the liquid or partially liquid stream 8, i.e. of the stream A2. The inert gas can thus make it possible to entrain in the gas phase at least some of said impurities C initially present in the stream A2. Alternatively, the inert gas can entrain in the gas phase said stream A3 comprising said hydrohalocarbon B and in which the content of impurities C has been reduced. Said pressurized distillation device 1 also comprises a first outlet 9 and a second outlet 11. Said first outlet 9 makes it possible to recover a gas stream 6. Said first outlet 9 can be positioned at the periphery or in the center of said device 1. Said second outlet 11 makes it possible to recover a liquid stream 12. Depending on said hydrohalocarbon considered and on said impurity or impurities present in said stream A2, said stream A3 comprising said hydrohalocarbon B can be recovered in gaseous form via said first outlet 9 (i.e. said stream A3 will be the gas stream 6) or via said second outlet 11 (i.e. said stream A3 will be said liquid stream 12). Thus, when said stream A3 is recovered in gaseous form via said first outlet 9, said stream A4 is recovered via said second outlet 11 in liquid form. Alternatively, when said stream A3 is recovered in liquid form via the second outlet 11, said stream A4 is recovered in gaseous form via said first outlet 9.

Said second outlet 11 can supply another rotating packed bed arranged on the same rotatable shaft or said second outlet 11 can supply another rotating packed bed operating at a different pressure. Said stream A2 is introduced into said rotating packed bed 2 and is distributed radially with respect to the rotatable shaft of the latter, that is to say radially with respect to the shaft 3. Preferably, said stream A2 is introduced parallel to the rotatable shaft of said rotating packed bed 2. In particular, said stream A2 is introduced parallel to the rotatable shaft 3 of said rotating packed bed 2 and is distributed radially with respect to the rotatable shaft of the latter, that is to say radially with respect to the shaft 3.

FIG. 2 illustrates a pressurized distillation device 1 comprising two rotating packed beds 2a, 2b. The pressurized distillation device 1 operates as described above in relation to FIG. 1. In this embodiment with two rotating packed beds arranged in cascade, the pressure is identical in the two beds 2a and 2b. The stream A2 introduced into the device 1 feeds the first rotating packed bed 2a then the second rotating packed bed 2b. Liquid flows from the first rotating packed bed 2a to the second rotating packed bed 2b through the device center 20. The gas stream 7 introduced through said second inlet 5 flows within the rotating packed bed 2b then through the device center 20, and through the rotating packed bed 2a in order to be recovered via the first outlet 9. The gas stream 7 will be concentrated in impurities C or in hydrohalocarbon. FIG. 3 also illustrates an embodiment in which the pressurized distillation device 1 comprises two rotating packed beds 2a, 2b. In this case represented in FIG. 3, the rotating packed beds 2a and 2b are configured in the form of two combs arranged in staggered rows. Preferably, only one of the two combs is rotatable. Preferably, packing is also present between the branches of the combs so as to increase the contact area. A person skilled in the art will adapt the shape and arrangement of the combs in order to maximize the separation performance of the various constituents. The liquid stream, for example the stream A2, introduced through the first inlet 10, flows into the first rotating packed bed 2a then to the second rotating packed bed 2b through the device center 20 in order to be recovered at the second outlet 11. The gas stream 7 follows the reverse path from the second inlet 5 to the first outlet 9.

FIG. 4 illustrates another embodiment in which the pressurized distillation device 1 comprises two rotating packed beds 2a and 2b. The two rotating packed beds 2a and 2b operate independently of one another. The temperature of each bed can be adjusted independently, as can the pressure. The liquid stream can be heated or cooled between each stage. The liquid stream can be introduced into one of the lower stages. In the embodiment specifically illustrated in FIG. 4, the pressurized distillation device 1 comprises a first stage 1a comprising a rotating packed bed 2a and a second stage 1b comprising a rotating packed bed 2b. Preferably, the pressure in the rotating packed bed 2a is different from that in the rotating packed bed 2b. Said rotating packed bed 2a is connected to a shaft 3a connected to a motor 4a (not shown) enabling the rotation of said rotating packed bed 2a around the shaft 3a. The shaft 3a and the motor 4a make it possible to regulate the speed of rotation of said rotating packed bed 2a. Said rotating packed bed 2b is connected to a shaft 3b connected to a motor 4b enabling the rotation of said rotating packed bed 2b around the shaft 3b. The shaft 3b and the motor 4b make it possible to regulate the speed of rotation of said rotating packed bed 2b. Said pressurized distillation device 1 also comprises a first inlet 10 for supplying the rotating packed bed 2a with a stream 8 that is liquid or at least partially liquid, preferably with said stream A2. Said pressurized distillation device 1 also comprises a second inlet 5a for supplying the rotating packed bed 2a with a stream 7a. The latter stream 7a is equivalent to stream 7 defined above. Said rotating packed bed 2a is connected to a first outlet 9a and a second outlet 11a. Said first outlet 9a makes it possible to recover a gas stream 6. Said second outlet 11a makes it possible to recover a liquid stream which supplies said rotating packed bed 2b. Said rotating packed bed 2b is connected to a third outlet 9b and a fourth outlet 11b. Said third outlet 9b makes it possible to recover a gas stream which supplies said rotating packed bed 2a. Said third outlet 9b may be connected to said second inlet 5a. Said fourth outlet 11b makes it possible to recover a liquid stream. The liquid stream 8 introduced through the first inlet 10 flows into the first stage 1a comprising the first rotating packed bed 2a then flows to the second stage comprising the second rotating packed bed 2b via the second outlet 11a in order to be recovered at the fourth outlet 11b. The second outlet 11a is preferably positioned so as to enable the introduction of the liquid stream at the center of the second rotating packed bed 2b. A person skilled in the art will adapt the shape and arrangement of the constituent elements of the pressurized distillation device in order to maximize its performance, for example by optimizing the flow of the streams A3 or A4 to the desired outlets. For example, in FIG. 4, the blocks 13a, 13b, 13c and 13d aim to promote the flow of the gas stream toward the outlets 9a and 9b. The flow rate of the liquid passing through the second outlet 11a can be adapted to prevent the gas from flowing through it and to promote the flow of the gas stream toward the third outlet 9b. Blocks 13 may also be present in the devices shown in FIGS. 1, 2 and 3 in order to force the gas stream 7 to pass through the packed bed. These blocks are not shown in FIGS. 1, 2 and 3 for the sake of clarity. It is known practice for those skilled in the art to position these blocks at the locations that make it possible to generate a pressure drop on the passage of the gas in order to force said gas to cross the rotating packed bed, irrespective of the device (FIGS. 1 to 4).

Depending on said hydrohalocarbon considered and on said impurity or impurities present in said stream A2, said stream A3 can be recovered in gaseous form via said first outlet 9a of the rotating packed bed 2a (i.e. said stream A3 will be the gas stream 6) or via said fourth outlet 11b of the rotating packed bed 2b (i.e. said stream A3 will be said liquid stream 12).

According to a preferred embodiment, the speed of said one or more rotating packed beds 2 is from 100 to 3000 rpm (revolutions per minute), advantageously from 200 to 2500 rpm, preferably from 500 to 2000 rpm. Preferably, the speed of said one or more rotating packed beds is chosen so as to prevent the stream A2 introduced thereinto from forming droplets on the packing. The speed of rotation is selected so that the thickness of the liquid film created in the packing is as small as possible without leading to the formation of a fog.

According to a preferred embodiment, step iii) is carried out at a pressure of from 2 to 200 bar absolute, preferably from 5 to 100 bar absolute, more preferentially from 5 to 40 bar absolute, in particular from 5 to 30 bar absolute.

According to a preferred embodiment, step iii) is carried out at a temperature of from 20° C. to 200° C., preferably from 30° C. to 175° C. and in particular from 40° C. to 150° C.

The temperature and pressure conditions depend on the constituents of said stream A2, i.e. of said hydrohalocarbon B present in the stream and on said at least one impurity present in said stream A2. Those skilled in the art will adapt the temperature and pressure conditions using their general knowledge.

The implementation of step iii) makes it possible to purify said stream A2 in order to obtain a stream A3 which comprises said hydrohalocarbon B and in which the content of said at least one impurity C is reduced relative to the content thereof in said stream A2. In particular, said stream A3 may be devoid of said at least one impurity C.

Said stream A3 comprises said hydrohalocarbon B initially contained in said stream A2.

Thus, said stream A3 comprises said hydrohalocarbon B selected from group B1 as defined above.

Preferably, said stream A3 comprises said hydrohalocarbon B selected from group B2 as defined above.

Preferably, said stream A3 comprises at least 20% by weight of said hydrohalocarbon B on the basis of the total weight of said stream. In particular, said stream A3 comprises at least 22%, at least 24%, at least 26%, at least 28%, at least 30%, at least 32%, at least 34%, at least 36%, at least 38%, at least 40%, at least 42%, at least 44%, at least 46%, at least 48%, at least 50%, at least 52%, at least 54%, at least 56%, at least 58%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 96%, at least 98% by weight of said hydrohalocarbon B on the basis of the total weight of said stream A3. Preferably, the content of said hydrohalocarbon B in said stream A3 is greater than the content of said hydrohalocarbon B in said stream A2.

Preferably, said stream A3 comprises less than 80% by weight of said at least one impurity C on the basis of the total weight of said stream. When said stream A3 comprises several impurities C, the content mentioned above is that of all the impurities C included in said stream A3. In particular, said stream A3 comprises less than 78%, less than 76%, less than 74%, less than 72%, less than 70%, less than 68%, less than 66%, less than 64%, less than 62%, less than 60%, less than 58%, less than 56%, less than 54%, less than 52%, less than 50%, less than 48%, less than 46%, less than 44%, less than 42%, less than 40%, less than 38%, less than 36%, less than 34%, less than 32%, less than 30%, less than 28%, less than 26%, less than 24%, less than 22%, less than 20%, less than 18%, less than 16%, less than 14%, less than 12%, less than 10%, less than 8%, less than 6%, less than 4%, less than 2% by weight of said at least one (of said) impurity (impurities) C on the basis of the total weight of said stream A3. Preferably, the content of said at least one (of said) impurity (impurities) C in said stream A3 is lower than the content of said at least one (of said) impurity (impurities) C in said stream A2. More particularly, said stream A3 is devoid of said at least one (of said) impurity (impurities) C. The term "devoid of" used here corresponds to a content of less than 0.5%, advantageously less than 0.1%, preferably less than 0.01%, more preferentially less than 0.001%, in particular less than 0.0001% by weight on the basis of the total weight of said stream. If necessary, said stream A3 can be additionally purified by techniques known to those skilled in the art (distillation, cold separation, absorption, adsorption).

Preferably, said stream A4 comprises said at least one (of said) impurity (impurities) C as defined in the present application.

Thus, said stream A4 comprises at least one impurity C selected from the group C1 as defined above.

Preferably, said stream A4 comprises at least two impurities C selected from the group C1 as defined above.

Preferably, said stream A4 comprises at least three, advantageously at least four, preferably at least five, more preferentially at least six, in particular at least seven, more particularly at least eight, favorably at least nine, preferentially favorably at least ten impurities C selected from the group C1 as defined above.

Preferably, said stream A4 comprises said at least one, advantageously at least two, preferably at least three, more preferentially at least four, in particular at least five, more particularly at least six, favorably at least seven, advantageously favorably at least eight, preferentially favorably at least nine, particularly favorably at least ten impurities C selected from the group C2 as defined above.

Preferably, said stream A4 comprises at least 20% by weight of said at least one, advantageously at least two, preferably at least three, more preferentially at least four, in particular at least five, more particularly at least six, favorably at least seven, advantageously favorably at least eight, preferentially favorably at least nine, particularly favorably at least ten impurities C on the basis of the total weight of said stream A4. In particular, said stream A4 comprises at least 22%, at least 24%, at least 26%, at least 28%, at least 30%, at least 32%, at least 34%, at least 36%, at least 38%, at least 40%, at least 42%, at least 44%, at least 46%, at least 48%, at least 50%, at least 52%, at least 54%, at least 56%, at least 58%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 96%, at least 98% by weight of said at least one, advantageously at least two, preferably at least three, more preferentially at least four, in particular at least five, more particularly at least six, favorably at least seven, advantageously favorably at least eight, preferentially favorably at least nine, particularly favorably at least ten impurities C on the basis of the total weight of said stream A4.

The present invention makes it possible to purify a stream comprising a hydrohalocarbon B as defined in the present application. After purification, said hydrohalocarbon B thus recovered can be used in processes for producing other hydrofluorocarbon compounds or can be used in applications such as blowing agents for the preparation of polyurethane or polystyrene foam, refrigerant compositions, heat-transfer compositions. Said impurity or impurities recovered in the stream A4 can also be reused in processes for preparing hydrofluorocarbon compounds or in refrigerant compositions or heat-transfer compositions.

The invention claimed is:

1. A process for purifying a composition comprising a hydrohalocarbon B comprising the steps of:
   i. providing a composition A1 comprising a hydrohalocarbon B and at least one impurity C different from said hydrohalocarbon B,
   ii. compressing said composition A1, and optionally cooling it, so as to obtain said hydrohalocarbon B in liquid form in order to form a liquid stream A2 comprising said hydrohalocarbon B,
   iii. distilling said stream A2 obtained in step ii) in order to form and recover a stream A3 comprising said hydrohalocarbon B and a stream A4 comprising said at least one impurity C wherein step iii) is carried out in a pressurized distillation device comprising one or more rotating packed beds.

2. The process as claimed in claim 1, wherein said stream A2 is introduced in liquid form into said one or more rotating packed beds and is distributed therein radially with respect to a rotatable shaft thereof.

3. The process as claimed in claim 1, wherein the speed of said one or more rotating packed beds is from 100 to 3000 revolutions per minute (rpm).

4. The process as claimed in claim 1, wherein step iii) is carried out at a pressure of from 2 to 200 bar absolute.

5. The process as claimed in claim 1, wherein said hydrohalocarbon B comprises three carbon atoms and at least one halogen atom.

6. The process as claimed in claim 1, wherein said hydrohalocarbon B is of formula (I) $CX(Y)_2-CX(Y)_m-CH_mXY$, where X and Y independently represent H, F or Cl and m=0 or 1 with at least one from among X or Y being Cl or F.

7. The process as claimed in claim 1, wherein said hydrohalocarbon B is selected from the group B1 consisting of 2,3,3,3-tetrafluoropropene, 2-chloro-3,3,3-trifluoropropene, 1,3,3,3-tetrafluoropropene, 1-chloro-3,3,3-trifluoropropene, 1,1,1,2,2-pentafluoropropane, 2-chloro-1,1,1,2-tetrafluoropropane, 2,3-dichloro-1,1,1-trifluoropropane, 3,3,3-trifluoropropene, 1,1,1,3,3-pentafluoropropane, 1,1,1,2,3-pentafluoropropane, 1,1,1,2,3-pentafluoropropene, 1,1,1,2,3-pentachloropropane, 1,1,2,2,3-pentachloropropane, 1,1,1,3,3-pentachloropropane, 1,1,2,3-tetrachloro-1-propene, 2,3,3,3-tetrachloro-1-propene, 1,1,3,3-tetrachloro-1-propene and 1,3,3,3-tetrachloro-1-propene.

8. The process as claimed in claim 1, wherein said at least one impurity C is selected from the group Cl consisting of chloromethane, dichloromethane, tetrachloromethane, trichlorofluoromethane, dichlorodifluoromethane, chlorotrifluoroethane, dichlorotetrafluoroethane, chloropentafluoroethane, fluoromethane, difluoromethane, trifluoromethane, fluoroethane, 1,1-difluoroethane, 1,2-difluoroethane, 1,1,1-trifluoroethane, 1,1,2-trifluoroethane, 3,3,3-trifluoropropyne, methane, ethane, propane, 1,1,1-trifluoroethane, 1,1,1,2,3,3,3-heptachloropropane, 1,1,1,2,2,3,3-heptachloropropane, 2-chloro-1,1,1,3,3,3-hexafluoropropane, 1-chloro-1,1,2,3,3,3-hexafluoropropane, 2-chloro-1,1,2,3,3,3-hexafluoropropane, 3-chloro-1,1,1,2,2,3-hexafluoropropane, 1-chloro-1,1,2,2,3,3-hexafluoropropane, 1,1,1,3,3,3-hexachloropropane, 1,1,1,2,3,3-hexachloropropane, 1,1,2,2,3,3-hexachloropropane, 1,1,1,2,2,3-hexachloropropane, 3-chloro-1,1,1,3,3-pentafluoropropane, 1-chloro-1,2,3,3,3-pentafluoropropane, 1-chloro-1,1,2,3,3-pentafluoropropane, 3-chloro-1,1,2,2,3-pentafluoropropane, 3-chloro-1,1,1,2,2-pentafluoropropane, 1-chloro-1,1,2,2,3-pentafluoropropane, 2-chloro-1,1,1,3,3-pentafluoropropane, 2-chloro-1,1,2,3,3-pentafluoropropane, 2-chloro-1,1,1,2,3-pentafluoropropane, 1,1,1,3,3,3-hexafluoropropane, 1,1,2,2,3,3-hexafluoropropane, 1,1,1,2,2,3-hexafluoropropane, 1,1,1,2,3,3-hexafluoropropane, 1,1,1,3,3-pentachloropropane, 1,1,2,3,3-pentachloropropane, 1,1,1,2,3-pentachloropropane, 1,1,2,2,3-pentachloropropane, 1,1,1,2,2-pentachloropropane, 1,1,2,2,3-pentafluoropropane, 1,1,1,2,2-pentafluoropropane, 1,1,2,3,3-pentafluoropropane, 1,1,1,2,3-pentafluoropropane, 1,1,1,3,3-pentafluoropropane, 1,1,3,3-tetrachloropropane, 1,1,1,3-tetrachloropropane, 1,1,2,3-tetrachloropropane, 1,1,1,2-tetrachloropropane, 1,2,2,3-tetrachloropropane, 1,1,2,2-tetrachloropropane, 1-chloro-1,1,3-trifluoropropane, 1-chloro-3,3,3-trifluoropropane, 1-chloro-1,1,3-trifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 1,1,3-trichloropropane, 1,1,1-trichloropropane, 1,2,3-trichloropropane, 1,1,2-trichloropropane, 1,2,2-trichloropropane, hexachloropropene, 1,1,2-trichloro-3,3,3-trifluoropropene, 1,2,3-trichloro-1,3,3-trifluoropropene, 2,3,3-trichloro-1,1,3-trifluoropropene, 3,3,3-trichloro-1,1,2-trifluoropropene, 1,3,3-trichloro-1,2,3-trifluoropropene, 1,1,3-trichloro-2,3,3-trifluoropropene, 3,3-dichloro-1,1,2,3-tetrafluoropropene, 2,3-dichloro-1,1,3,3-tetrafluoropropene, 1,3-dichloro-1,2,3,3-tetrafluoropropene, 1,2-dichloro-1,3,3,3-tetrafluoropropene, 1,2-dichloro-2,3,3,3-tetrafluoropropene, hexafluoropropene, 1,1,2,3,3-pentachloropropene, 1,2,3,3,3-pentachloropropene, 1,1,3,3,3-pentachloropropene, 1,2-dichloro-3,3,3-trifluoropropene, 2,3-dichloro-1,3,3-trifluoropropene, 2,3-dichloro-1,1,3-trifluoropropene, 3,3-dichloro-1,1,3-trifluoropropene, 1,3-dichloro-1,3,3-trifluoropropene, 1,1-dichloro-3,3,3-trifluoropropene, 1,1-dichloro-2,3,3-trifluoropropene, 1,3-dichloro-2,3,3-trifluoropropene, 3,3-dichloro-1,2,3-trifluoropropene, 3,3-dichloro-1,1,2-trifluoropropene, 3-chloro-1,2,3-tetrafluoropropene, 2-chloro-1,1,3,3-tetrafluoropropene, 3-chloro-1,1,3,3-tetrafluoropropene, 1-chloro-1,2,3,3-tetrafluoropropene, 1-chloro-1,3,3,3-tetrafluoropropene, 3-chloro-1,2,3,3-tetrafluoropropene, 2-chloro-1,3,3,3-tetrafluoropropene, 1-chloro-2,3,3,3-tetrafluoropropene, 1,1,3,3,3-pentafluoropropene, 1,1,2,3,3-pentafluoropropene, 1,2,3,3,3-pentafluoropropene, 1,1,2,3-tetrachloropropene, 1,2,3,3-tetrachloropropene, 2,3,3,3-tetrachloropropene, 1,1,3,3-tetrachloropropene, 1,3,3,3-tetrachloropropene, 2-chloro-3,3,3-trifluoropropene, 3-chloro-2,3,3-trifluoropropene, 1-chloro-2,3,3-trifluoropropene, 1-chloro-3,3,3-trifluoropropene, 2-chloro-1,3,3-trifluoropropene, 3-chloro-1,2,3-trifluoropropene, 3-chloro-1,3,3-trifluoropropene, 3-chloro-1,1,2-trifluoropropene, 2-chloro-1,1,3-trifluoropropene, 3-chloro-1,1,3-trifluoropropene, 1-chloro-1,2,3-trifluoropropene, 1-chloro-1,3,3-trifluoropropene, 2,3,3,3-tetrafluoropropene, 1,3,3,3-tetrafluoropropene, 1,1,2,3-tetrafluoropropene, 1,1,3,3-tetrafluoropropene, 1,2,3,3-tetrafluoropropene, 1,1,2-trichloropropene, 1,2,3-trichloropropene, 2,3,3-trichloropropene, 1,1,3-trichloropropene, 1,3,3-trichloropropene, 3,3,3-trichloropropene, 3-chloro-3,3-difluoropropene, 3-chloro-2,3-difluoropropene, 2-chloro-3,3-difluoropropene, 2-chloro-1,1-difluoropropene, 3-chloro-1,1-difluoropropene, 3-chloro-1,2-difluoropropene, 2-chloro-1,3-difluoropropene, 3-chloro-1,3-difluoropropene, 1-chloro-2,3-difluoropropene, 1-chloro-3,3-difluoropropene, 1,1,3-trifluoropropene, 1,1,2-trifluoropropene, 3,3,3-trifluoropropene, 1,2,3-trifluoropropene, 2,3,3-trifluoropropene, 1,3,3-trifluoropropene, 1,1-dichloropropene, 1,2-dichloropropene, 2,3-dichloropropene, 1,3-dichloropropene, 3,3-dichloropropene, 1,1-difluoropropene, 1,2-difluoropropene, 2,3-difluoropropene and 3,3-difluoropropene.

9. The process as claimed in claim 1, wherein said stream A3 comprises said hydrohalocarbon B in a weight content of greater than 90% by weight on the basis of the total weight of said stream A3.

10. The process as claimed in claim 1, wherein in said stream A3 the content of said at least one impurity C is less than 1% by weight.

11. The process as claimed in claim 1, wherein said pressurized distillation device comprises an inlet enabling said pressurized distillation device to be fed with a stream sweeping said rotating packed bed countercurrently, wherein said sweeping stream comprises a solvent or inert gas.

* * * * *